US008168420B2

(12) United States Patent
Takagi et al.

(10) Patent No.: US 8,168,420 B2
(45) Date of Patent: May 1, 2012

(54) MICROORGANISM CAPABLE OF MICROBIALLY DECOMPOSING CHLORO-, METHYLTHIO- AND METHOXY-TRIAZINE AGRICHEMICALS

(75) Inventors: Kazuhiro Takagi, Tsukuba (JP); Kunihiko Fujii, Tsukuba (JP); Naoki Harada, Tsukuba (JP); Akio Iwasaki, Tsukuba (JP)

(73) Assignee: Kowa Company, Ltd., Nagoya-shi (JP)

( * ) Notice: Subject to any disclaimer, the term of this patent is extended or adjusted under 35 U.S.C. 154(b) by 316 days.

(21) Appl. No.: 12/513,573

(22) PCT Filed: Nov. 20, 2007

(86) PCT No.: PCT/JP2007/001269
§ 371 (c)(1),
(2), (4) Date: May 5, 2009

(87) PCT Pub. No.: WO2008/062557
PCT Pub. Date: May 29, 2008

(65) Prior Publication Data
US 2010/0068788 A1    Mar. 18, 2010

(30) Foreign Application Priority Data
Nov. 21, 2006  (JP) ................................. 2006-314187

(51) Int. Cl.
*C12N 1/20* (2006.01)
*C02F 3/34* (2006.01)
*A62D 3/02* (2007.01)

(52) U.S. Cl. .................. 435/252.1; 435/262; 435/262.5; 435/822

(58) Field of Classification Search .................... None
See application file for complete search history.

(56) References Cited

FOREIGN PATENT DOCUMENTS
JP    2005-027536 A    2/2005

OTHER PUBLICATIONS

Topp et al. Applied and Environmental Microbiology. Aug. 2000, vol. 66, No. 8, pp. 3134-3141.*
Nir Sapir et al. "Substrate specificity and colorimetric assay for recombinant TrzN derived from *Arthrobacter aurescens* TC1". Applied and Environmental Microbiology. May 2005, vol. 71, No. 5, pp. 2214-2220.*

S. Piutti et al; "Isolation and characterisation of *Nocardioides* sp. SP12, an atrazine-degrading bacterial strain possessing the gene trzN from bulk- and maize rhizosphere soil," FEMS Microbiol. Lett; 2003; vol. 221; No. 1; pp. 111-117.
K. Satsuma "Characterisation of new strains of atrazine-degrading *Nocardioides* sp. isolated from Japanese riverbed sediment using naturally derived river ecosystem," Pest. Manag. Sci.; Apr. 2006; vol. 62; No. 4; pp. 340-349.
E. Topp "Characterisation of S-triazine herbicide metabolism by a *Nocardioides* sp. isolated form agricultural soils," Appl. Environ. Microbiol. 2000; vol. 66; No. 8; pp. 3134-3141.
Database EMBL [Online ] Nov. 6, 1997. "Nocarxioodes Jensenil 16S ribosomal RNA gene, partial sequence." Retrieved from EBI accession No. EMBL: AF005006; Database accession No. AF005006. XP-002602035.
Yamazaki, Kenichi et al.; "Different substrate specificities of two triazine hydrolases (TrzNs) from *Nocardioides* species"; Sep. 2008, FEMS Microbiology Letters Sep. 2008 LNKD-PUBMED: 18671800, vol. 286, NR. 2., pp. 171-177, XP002601975.
Cook et al., "Ametryne and Prometryne as Sulfur Sources for Bacteria", Applied and Environmental Microbiology, 1982, pp. 781-786, vol. 43, No. 4.
Seffernick et al., "Substrate Specificity of Atrazine Chlorohydrolase and Atrazine-Catabolizing Bacteria", Applied and Environmental Microbiology, 2000, pp. 4247-4252, vol. 66, No. 10.
Strong et al., "*Arthrobacter aurescens* TC1 Metabolizes Diverse s-Triazine Ring Compounds", Applied and Environmental Microbiology, 2002, pp. 5973-5980, vol. 68, No. 12.

* cited by examiner

*Primary Examiner* — Vera Afremova
(74) *Attorney, Agent, or Firm* — Westerman, Hattori, Daniels & Adrian, LLP

(57) ABSTRACT

Disclosed are: a novel microorganism which can decompose a methylthiotriazine compound (particularly, simetryn, dimethametryn, prometryn), a chlorotriazine compound (particularly, simazine, atrazine, propazine) and a methoxytriazine compound (particularly, simeton, atraton, prometon) which have been frequently used as agrichemicals or the like; and a method for decomposing a methylthiotriazine compound, a chlorotriazine compound and/or a methoxytriazine compound by using the microorganism. Specifically disclosed are: a novel bacterium *Nocardioides* sp. strain MTD22 which is capable of decomposing a methylthiotriazine compound, a chlorotriazine compound and a methoxytriazine compound; and a method for decomposing a methylthiotriazine compound, a chlorotriazine compound and/or a methoxytriazine compound, particularly simetryn, dimethametryn, prometryn, simazine, atrazine, propazine, simeton, atraton and/or prometon, by using the microorganism.

16 Claims, 2 Drawing Sheets

[FIG.1]
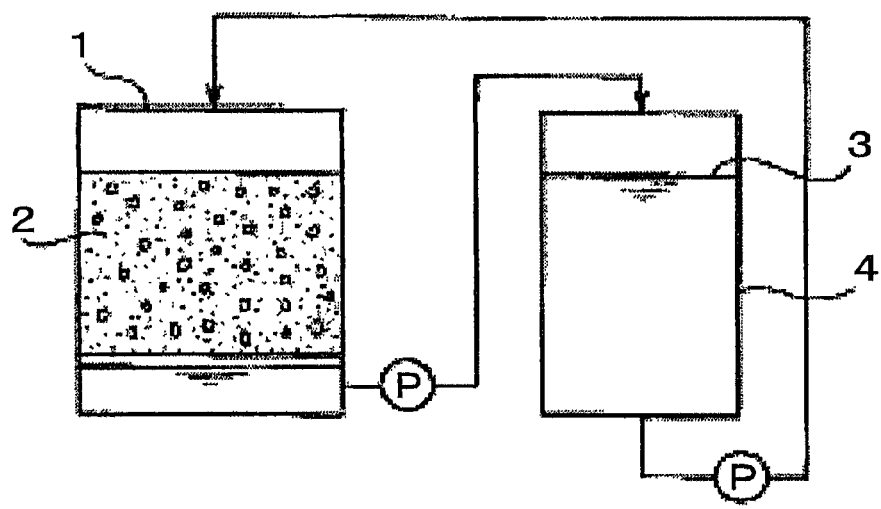
[FIG.2]
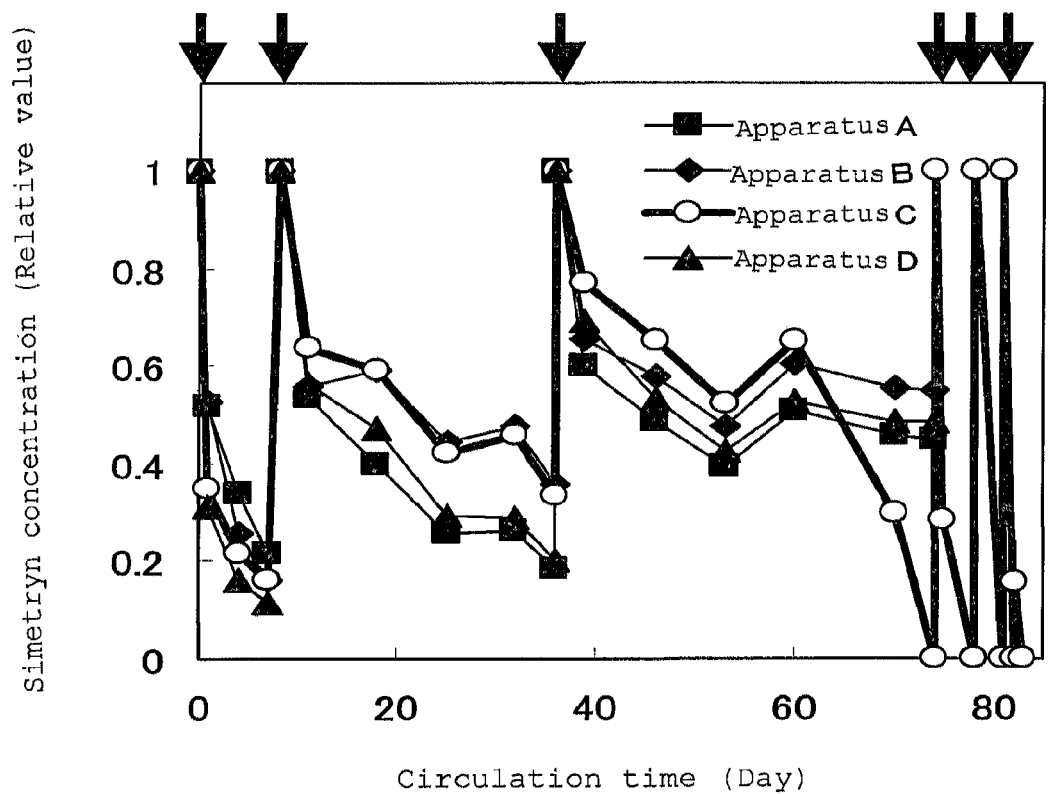

[FIG.3]
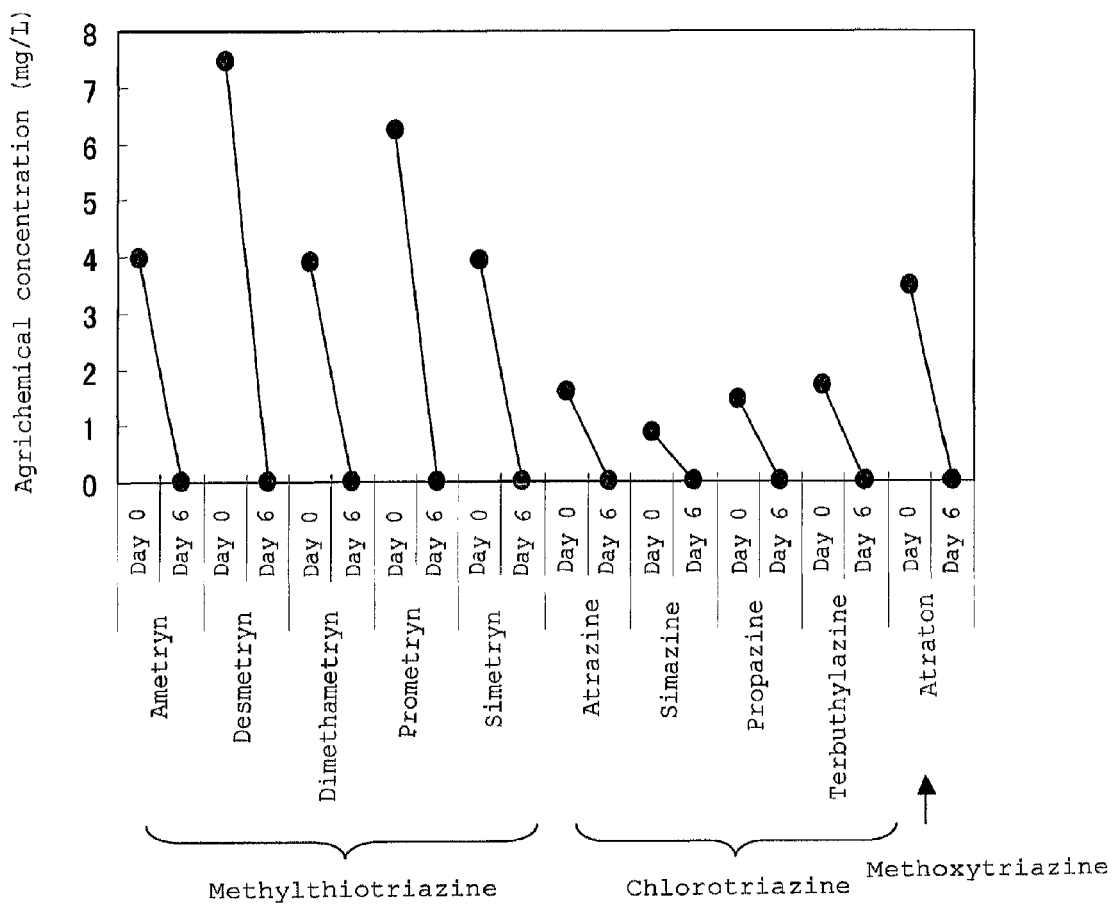

SEQUENCE LISTING

```
<160> NUMBER OF SEQ ID NOS: 1

<210> SEQ ID NO 1
<211> LENGTH: 1477
<212> TYPE: DNA
<213> ORGANISM: Nocardioides sp. MTD22

<400> SEQUENCE: 1
gacgaacgct ggcggcgtgc ttaacacatg caagtcgagc ggtaaggctc cttcgggagt        60
```

-continued

```
acacgagcgg cgaacgggtg agtaacacgt gagcaatctg cccttcacat cgggataacc      120 cccgaaacg  ggagctaata ccggatacga ccacttcagg catctgatgg tggtggaaag      180
ttccggcggt ggaggatgag ctcgcggcct atcagcttgt tggtgaggta atggctcacc      240
aaggcttcga cgggtagccg gcctgagagg gtgaccggcc acactgggac tgagacacgg      300
cccagactcc tacgggaggc agcagtgggg aatattggac aatgggcgaa agcctgatcc      360
agcaacgccg cgtgagggat gacggccttc gggttgtaaa cctctttcag cagggacgaa      420
gcgcaagtga cggtacctgc agaagaagca ccggccaact acgtgccagc agccgcggta      480
atacgtaggg tgcgagcgtt gtccggaatt attgggcgta aagggctcgt aggcggtctg      540
ttgcgtcggg agtgaaaact cagggcttaa ccctgagcct gcttccgata cgggcagact      600
agaggtatgc aggggagaac ggaattcctg gtgtagcggt gaaatgcgca gatatcagga      660
ggaacaccgg tggcgaaggc ggttctctgg gcattacctg acgctgagga gcgaaagtgt      720
ggggagcgaa caggattaga taccctggta gtccacaccg taaacgttgg gcgctaggtg      780
tgggactcat tccacgagtt ccgtgccgca gctaacgcat taagcgcccc gcctggggag      840 tacgccgca  aggctaaaac tcaaaggaat tgacgggggc ccgcacaagc ggcggagcat      900
gcggattaat tcgatgcaac gcgaagaacc ttacctaggt ttgacatata cgagaatccc      960
ctggagacag gggcctcttt ggacacttgt atacaggtgg tgcatggctg tcgtcagctc     1020
gtgtcgtgag atgttgggtt aagtcccgca acgagcgcaa ccctcgtctt atgttgccag     1080
cacgtcatgg tggggactca taagagactg ccggggtcaa ctcggaggaa ggtggggatg     1140
acgtcaagtc atcatgcccc ttatgcctag ggcttcacgc atgctacaat ggccggtaca     1200
aagggctgcg ataccgcaag gtggagcgaa tcccaaaaag ccggtctcag ttcggattgg     1260
ggtctgcaac tcgaccccat gaagtcggag tcgctagtaa tcgcagatca gcaacgctgc     1320
ggtgaatacg ttcccgggcc ttgtacacac cgcccgtcac gtcacgaaag ttggcaacac     1380
ccgaagccag tggcccaacc gtttacgagg ggagctgtcg aaggtggggc gagcgattgg     1440
gacgaagtcg taacaaggta gccgtaccgg aaggtgc                              1477
```

MICROORGANISM CAPABLE OF MICROBIALLY DECOMPOSING CHLORO-, METHYLTHIO- AND METHOXY-TRIAZINE AGRICHEMICALS

TECHNICAL FIELD

The present invention relates to a novel microorganism having the ability to decompose at least one selected from the group consisting of methylthiotriazine compounds (simetryn, ametryn, prometryn, dimethametryn, desmetryn, and terbutryn), chlorotriazine compounds (simazine, atrazine, propazine, and terbuthylazine), and methoxytriazine compounds (simeton, atraton, and prometon). More specifically, the present invention relates to a microorganism belonging to the genus *Nocardioides* and a method for decomposing such a triazine compound as described above using the microorganism or a complex microbial system containing the microorganism.

BACKGROUND ART

In modern agriculture, agrichemicals are absolutely necessary to maintain stable crop yields and reduce the amount of labor and production cost. However, it has been revealed that agrichemicals used partially flow into rivers, lakes, groundwater, service water, etc., and therefore there is concern about the influence of agrichemicals on organisms in the general environment. Among various types of microorganisms living in soil, some microorganisms have the ability to decompose and detoxify organic chemicals such as agrichemicals. However, the density of such decomposing bacteria in the natural environment is low, and in addition, the decomposing bacteria are not uniformly distributed in the natural environment. Therefore, it is usually impossible to prevent the accumulation and dispersion of organic pollutants in the environment before they happen. Under the circumstances, decomposition of organic pollutants such as agrichemicals using decomposing soil bacteria selectively enriched and isolated, that is, so-called bioremediation, can be considered effective.

Triazine compounds have been heavily used as agrichemicals, defoaming agents, and dyes throughout the world for a long time, but are now regarded as problematic environmental pollutants. It has been already known that atrazine, which is a chlorotriazine agrichemical, can be decomposed by many kinds of microorganisms (see Patent Document 1). However, methylthiotriazine agrichemicals such as simetryn and methoxytriazine agrichemicals such as simeton are more difficult to decompose, and therefore reports about the microbial decomposition of methylthiotriazines and methoxytriazines are limited. For example, Cook and Hutter have reported that decomposing soil bacteria were enriched by using a synthetic medium containing ametryn or prometryn as a sulfur source, and then three kinds of the bacteria showing a higher growth rate were finally selected (see Non-Patent Document 1). According to this report, two of the three kinds of bacteria decomposed ametryn so that a demethylthiolated metabolite was generated, and the other one decomposed ametryn and prometryn so that demethylthiolated metabolites were generated. However, in this report, there is no description about the bacteriological studies of these strains. Further, Strong et al. have reported that *Arthrobacter aurescens* strain TC1 having the ability to decompose atrazine was isolated from a dump-site polluted with a high level of atrazine and the *Arthrobacter aurescens* strain TC1 grew in a medium containing ametryn or prometryn as the sole source of nitrogen (see Non-Patent Document 2). Further, Shapir et al. have reported that ametryn was decomposed by an enzyme obtained by expressing an *Arthrobacter aurescens* strain TC1-derived atrazine-degrading enzyme gene spliced into *E. coli* (see Non-Patent Document 3) . Further, Topp et al. have reported that when dispersed in solutions each containing simetryn, ametryn, prometryn, or terbutryn and statically incubated under an anaerobic condition, whole cells or cell extracts of *Nocardioides* sp. strain C190 decomposed simetryn, ametryn, prometryn, and terbutryn so that demethylthiolated metabolites were generated (see Non-Patent Document 4). Further, Seffernick et al. have reported that ametryn was demethylthiolated by cell extracts of *Clavibacter michiganensis* strain ATZ1 (see Non-Patent Document 5).

As described above, there are some reports about the microbial decomposition of triazine compounds, but some of the isolated strains have not been sufficiently bacteriologically studied or need another carbon source to decompose a triazine compound and some of the reports have not shown the decomposition or decomposition rates of triazine compounds by living bacterial cells. For this reason, under the present circumstances, it is difficult to say that these strains can be practically used for bioremediation at this time.

Patent Document 1: Japanese Patent Application Laid-Open No. 2005-27536

Non-Patent Document 1: Cook, A. M., Hutter, R. 1982. Appl. Environ. Microbiol. 43, 781-786

Non-Patent Document 2: Strong, L. C., Rosendahl, C., Johnson, G., Sadowsky, M. J., Wackett, L. P. 2002. Appl. Environ. Microbiol. 68, 5973-5980

Non-Patent Document 3: Shapir, N., Rosendahl, C., Johnson, G., Andreina, M., Sadowsky, M. J., Wackett, L. P., 2005. Appl. Environ. Microbiol. 71, 2214-2220

Non-Patent Document 4: Topp, E., Mulbry, W. M., Zhu, H., Nour, S. M., Cuppels, D. 2000. Appl. Environ. Microbiol. 66, 3134-3141

Non-Patent Document 5: Seffernick, J. L., Johnson, G., Sadowsky, M. J. Wackett, L. P. 2000. Appl. Environ. Microbiol. 66, 4247-4252

DISCLOSURE OF THE INVENTION

Problems to be Solved by the Invention

It is an object of the present invention to provide a novel microorganism capable of decomposing a methylthiotriazine compound such as simetryn, ametryn, prometryn, dimethametryn, desmetryn, or terbutryn, a chlorotriazine compound such as simazine, atrazine, propazine, or terbuthylazine, and a methoxytriazine compound such as simeton, atraton, or prometon and a method for decomposing a methylthiotriazine compound, a chlorotriazine compound and/or a methoxytriazine compound using the novel microorganism.

Means for Solving the Problems

The present inventors have isolated a bacterium belonging to the genus *Nocardioides* from soil and have found that the bacterium has the ability to decompose a methylthiotriazine compound, a chlorotriazine compound, and a methoxytriazine compound. Further, the present inventors have examined the biological characteristics of the bacterium and have found that the bacterium is a novel bacterium having a distinctive 16S rRNA gene. Further, the present inventors have found that the use of a single strain of this bacterium makes it possible to efficiently decompose a chlorotriazine compound in addition to a methylthiotriazine compound such as simetryn and a methoxytriazine compound which are inherently difficult to decompose.

The present invention provides the following [1] to [13].

[1] A bacterium belonging to the genus *Nocardioides* which has an ability to decompose a methylthiotriazine compound, a chlorotriazine compound, and a methoxytriazine compound.

[2] The bacterium according to the above [1], wherein the methylthiotriazine compound is at least one selected from the group consisting of simetryn, ametryn, prometryn, dimethametryn, desmetryn, and terbutryn.

[3] The bacterium according to the above [1] or [2], wherein the chlorotriazine compound is at least one selected from the group consisting of simazine, atrazine, propazine, and terbuthylazine.

[4] The bacterium according to any one of the above [1] to [3], wherein the methoxytriazine compound is at least one selected from the group consisting of simeton, atraton, and prometon.

[5] A bacterium belonging to the genus *Nocardioides* which has a 16S rRNA gene containing the following (A) or (B):

(A) a DNA comprising the base sequence set forth in SEQ ID NO:1, or (B) a DNA having an identity of 95% or more with the base sequence set forth in SEQ ID NO:1, and has an ability to decompose a methylthiotriazine compound, a chlorotriazine compound, and a methoxytriazine compound.

[6] *Nocardioides* sp. strain MTD22 (accession number: FERM P-20989; accession number FERM BP-10849) having an ability to decompose a methylthiotriazine compound, a chlorotriazine compound, and a methoxytriazine compound.

[7] A method for decomposing a methylthiotriazine compound, a chlorotriazine compound, and/or a methoxytriazine compound using the bacterium according to any one of the above [1] to [6].

[8] The decomposing method according to the above [7], wherein the methylthiotriazine compound is at least one selected from the group consisting of simetryn, ametryn, dimethametryn, desmetryn, terbutryn, and prometryn.

[9] The decomposing method according to the above [7] or [8], wherein the chlorotriazine compound is at least one selected from the group consisting of atrazine, simazine, propazine, and terbuthylazine.

[10] The decomposing method according to any one of the above [7] to [9], wherein the methoxytriazine compound is at least one selected from the group consisting of atraton, simeton, and prometon.

[11] A method for cleaning up soil, groundwater, and/or service water polluted with a methylthiotriazine compound, a chlorotriazine compound, and/or a methoxytriazine compound using the bacterium according to any one of the above [1] to [6].

[12] A triazine compound-decomposing agent for decomposing a methylthiotriazine compound, a chlorotriazine compound, and/or a methoxytriazine compound, which includes at least one bacterium according to any one of the above [1] to [6] and a carrier allowing the bacterium to grow.

[13] An agent for cleaning up soil, groundwater, and/or service water polluted with a methylthiotriazine compound, a chlorotriazine compound, and/or a methoxytriazine compound, which includes at least one bacterium according to any one of the above [1] to [6] and a carrier allowing the bacterium to grow.

That is, the present invention relates to a bacterium belonging to the genus *Nocardioides* which has the ability to decompose a methylthiotriazine compound, a chlorotriazine compound, and a methoxytriazine compound, preferably simetryn, ametryn, prometryn, dimethametryn, desmetryn, terbutryn, simazine, atrazine, propazine, terbuthylazine, simeton, atraton, and prometon. More specifically, the present invention relates to a bacterium belonging to the genus *Nocardioides* which has the ability to decompose a methylthiotriazine compound, a chlorotriazine compound, and a methoxytriazine compound, preferably simetryn, ametryn, prometryn, dimethametryn, desmetryn, terbutryn, simazine, atrazine, propazine, terbuthylazine, simeton, atraton, and prometon, and has a 16S rRNA gene having a base sequence set forth in SEQ ID NO:1 or a base sequence having an identity of 95% or more with the base sequence set forth in SEQ ID NO:1 modified by deletion, substitution, or addition of one or more bases without impairing the ability to decompose a methylthiotriazine compound, a chlorotriazine compound, and a methoxytriazine compound. A specific example of such a triazine-decomposing bacterium belonging to the genus *Nocardioides* includes a *Nocardioides* sp. strain MTD22 (FERM P-20989; FERM BP-10849).

As described above, the present invention provides a bacterium belonging to the genus *Nocardioides* which has the ability to decompose a methylthiotriazine compound, a chlorotriazine compound, and a methoxytriazine compound. A preferred example of such a bacterium includes a bacterium belonging to the genus *Nocardioides* which has a 16S rRNA gene containing the following (A) or (B):

(A) a DNA comprising the base sequence set forth in SEQ ID NO:1, or (B) a DNA having an identity of 95% or more with the base sequence set forth in SEQ ID NO:1, and has the ability to decompose a methylthiotriazine compound, a chlorotriazine compound, and a methoxytriazine compound. The sequence identity is preferably 95% or higher, more preferably 96% or higher, even more preferably 97% or higher, even more preferably 98% or higher, even more preferably 99% or higher, particularly preferably 99.5% or higher, more particularly preferably 99.8% or higher, and even more particularly preferably 99.9% or higher. An example of such a bacterium includes a *Nocardioides* sp. strain MTD22 (FERM P-20989; FERM BP-10849).

Further, the present invention also relates to a method for decomposing a methylthiotriazine compound, a chlorotriazine compound, and/or a methoxytriazine compound using a bacterium belonging to the genus *Nocardioides* which has the ability to decompose a methylthiotriazine, a chlorotriazine, and a methoxytriazine.

Further, the present invention also relates to a composition for decomposing a methylthiotriazine compound, a chlorotriazine compound, and/or a methoxytriazine compound (i.e., a triazine compound-decomposing agent), which includes a bacterium belonging to the genus *Nocardioides* having the ability to decompose a methylthiotriazine, a chlorotriazine, and a methoxytriazine and a carrier allowing the bacterium to grow.

Further, the present invention also relates to a method for cleaning up an environment containing a methylthiotriazine compound, a chlorotriazine compound, and/or a methoxytriazine compound using a bacterium belonging to the genus *Nocardioides* which has the ability to decompose a methylthiotriazine, a chlorotriazine, and a methoxytriazine.

In the present invention, the phrase "cleaning up an environment" means so-called bioremediation, and more specifically means the removal of chemicals difficult to decompose from, for example, contaminated soil, groundwater, and/or service water by decomposing the chemicals.

Further, the present invention also relates to a composition for cleaning up an environment containing a methylthiotriazine compound, a chlorotriazine compound, and/or a methoxytriazine compound, which includes a bacterium belonging to the genus *Nocardioides* having the ability to decompose a methylthiotriazine, a chlorotriazine, and a methoxytriazine and a carrier allowing the bacterium to grow.

EFFECTS OF THE INVENTION

The use of the methylthiotriazine-, chlorotriazine-, and methoxytriazine-decomposing bacterium according to the present invention makes it possible to decompose a methylthiotriazine compound, a chlorotriazine compound, and/or a methoxytriazine compound. Further, the use of the bacterium according to the present invention makes it possible to quickly decompose such a triazine compound and therefore to quickly and efficiently decompose waste agrichemicals or agrichemicals remaining in an environment. That is, the present invention provides a novel means for cleaning up an environment polluted with a triazine compound, that is, a novel means for bioremediation.

BRIEF DESCRIPTION OF THE DRAWINGS

FIG. 1 is a schematic view of an apparatus for the enrichment of a decomposing bacterium according to the present invention;

FIG. 2 is a graph showing a change in the concentration of simetryn in a circulating solution in each of the apparatuses A to D shown in FIG. 1; and FIG. 3 is a graph showing the result of a decomposition test of triazine compounds carried out in Example 3 using the decomposing bacterium strain MTD22 according to the present invention.

BEST MODE FOR CARRYING OUT THE INVENTION

Hereinafter, an embodiment of the present invention will be described. The present invention provides a methylthiotriazine-, chlorotriazine-, and methoxytriazine-decomposing bacterium isolated from soil. In the present invention, methylthiotriazine refers to a methylthiotriazine compound having a methylthio group in its triazine skeleton. Preferred examples of such a methylthiotriazine include simetryn (2,4-bis(ethylamino)-6-methylthio-s-triazine), dimethametryn (2-(1,2-dimethylpropylamino)-4-ethylamino-6-methylthio-s-tr iazine), prometryn (2,4-bis(isopropylamino)-6-methylthio-s-triazine), ametryn (2-ethylamino-4-isopropylamino-6-methylthio-s-triazine), desmetryn (2-isopropylamino-4-methylamino-6-methylthio-s-triazine), terbutryn (2-tert-butylamino-4-ethylamino-6-methylthio-s-triazine), and methoprotryn (2-isopropylamino-4-(3-methoxypropyl)-6-methylthio-s-triazi ne). Further, in the present invention, chlorotriazine refers to a chlorotriazine compound having a chloro group in its triazine skeleton. Preferred examples of such a chlorotriazine include simazine (2-chloro-4,6-bis(ethylamino)-s-triazine), atrazine (2-chloro-4-ethylamino-6-isopropylamino-s-triazine), propazine (2-chloro-4,6-bis(isopropylamino)-s-triazine), terbuthylazine (2-tert-butylamino-4-chloro-6-ethylamino-s-triazine), cyanazine (2-(1-cyano-1-methylethylamino)-4-ethylamino-6-chloro-s-tri azine), cyprazine (2-chloro-4-cyclopropylamino-6-isopropylamino-s-triazine), trietazine (2-chloro-4-diethylamino-6-ethylamino-s-triazine), norazine (2-chloro-4-isopropylamino-6-methylamino-s-triazine), ipazine (2-chloro-4-diethylamino-6-isopropylamino-s-triazine), proglinazine-ethyl (2-chloro-6-ethoxycarbonylmethylamino-4-isopropylamino-s-tr iazine), chlorazine (2-chloro-4,6-bis(diethylamino)-s-triazine), sebuthylazine (2-sec-butylamino-4-chloro-6-ethylamino-s-triazine), MPMT (4,6-bis(3-methoxypropylamino)-2-methylthio-s-triazine), and SD-15417 (2-chloro-4-(1-cyano-isopropylamino)-6-methylamino-s-triazi ne).

Further, in the present invention, methoxytriazine refers to a methoxytriazine compound having a methoxy group in its triazine skeleton. Preferred examples of such a methoxytriazine include atraton (2-ethylamino-4-isopropylamino-6-methoxy-s-triazine), simeton (2,4-bis(ethylamino)-6-methoxy-s-triazine), ipaton (2-diethylamino-4-isopropylamino-6-methoxy-s-triazine), noraton (2-isopropylamino-4-methylamino-6-methoxy-s-triazine), prometon (2,4-bis(isopropylamino)-6-methoxy-s-triazine), secbumeton (2-sec-butylamino-4-ethylamino-6-methoxy-s-triazine), methometon (2-methoxy-4,6-bis(3-methoxypropylamino)-s-triazine), and terbumeton (2-tert-butylamino-4-ethylamino-6-methoxy-s-triazine).

The bacterium according to the present invention belonging to the genus *Nocardioides* having the ability to decompose a methylthiotriazine, a chlorotriazine, and a methoxytriazine has the following bacteriological characteristics.

A. Morphological characteristics (culture medium: R2A agar (manufactured by Difco), incubation temperature: 30° C., incubation time: 48 hours)
 (1) Cell morphology: cocci
 (2) Size: 1.0 to 1.2 μm (diameter)
 (3) Spore formation: None
 (4) Mobility: None B. Colony morphology (culture medium: R2A agar (manufactured by Difco), incubation temperature: 30° C., incubation time: 48 hours)
 (1) Colony diameter: 1.0 mm
 (2) Color: Slightly yellow
 (3) Shape: Circular
 (4) Elevation: Lens shape
 (5) Margin: Entire
 (6) Surface profile: Smooth
 (7) Transparency: Opaque
 (8) Viscosity: Butter-like C. Physiological properties
 (1) Gram stain: +
 (2) Growth at 37° C.: −
 (3) Growth at 25° C.: +
 (4) Catalase: +
 (5) Oxidase: −
 (6) Acid/gas generation from glucose: −/−
 (7) 0/F test: −/−

D. Biochemical property tests (performed using API Coryne manufactured by SYSMEX bioMerieux Co., Ltd.)
 (1) Nitrate reduction: −
 (2) Pyrazine amidase: +
 (3) Pyrrolidonyl arylamidase: −
 (4) Alkaline phosphatase: −
 (5) β-glucuronidase: −
 (6) β-galactosidase: −
 (7) α-glucosidase: +
 (8) N-acetyl-β-glucosaminidase: −
 (9) Esculin: +
 (10) Urease: −
 (11) Gelatin hydrolysis: +
 (12) Glucose assimilation: −
 (13) Ribose assimilation: −

(14) Xylose assimilation: −
(15) Mannitol assimilation: −
(16) Maltose assimilation: −
(17) Lactose assimilation: −
(18) Sucrose assimilation: −
(19) Glycogen assimilation −

A specific example of the methylthiotriazine-, chlorotriazine-, and methoxytriazine-decomposing bacterium includes a novel bacterial isolate, *Nocardioides* sp. strain MTD22. The *Nocardioides* sp. strain MTD22 was deposited on Aug. 11, 2006 in the International Patent Organism Depositary of the National Institute of Advanced Industrial Science and Technology (Tsukuba Central 6, 1-1, Higashi 1-chome, Tsukuba-shi, Ibaraki, Japan) under the designation of microorganism "*Nocardioides* sp. strain MTD22" (identification reference given by the depositor) and the accession number "FERN P-20989", and then transferred on Jul. 4, 2007 to the International Depositary Authority and assigned the accession number "FERN BP-10849".

The present inventors have isolated the novel strain MTD22 capable of decomposing a methylthiotriazine, a chlorotriazine, and a methoxytriazine by a method which will be described later in Example 1. A medium suitable for decomposition of a triazine compound by this microorganism is shown in Table 1.

TABLE 1

| Composition of Inorganic Medium 1 | |
|---|---|
| $Na_2HPO_4 \cdot 12H_2O$ | 1.2 g |
| $KH_2PO_4$ | 0.5 g |
| $NH_4NO_3$ | 0.5 g |
| Trace element solution | 10 mL |
| Mixed vitamin solution | 1 mL |
| Water | 1000 mL |

The composition of the trace element solution shown in Table 1 is shown in the following Table 2.

TABLE 2

| Composition of Trace Element Solution | |
|---|---|
| EDTA·2Na | 500 mg |
| $MgSO_4 \cdot 7H_2O$ | 2000 mg |
| $FeSO_4 \cdot 7H_2O$ | 200 mg |
| $ZnSO_4 \cdot 7H_2O$ | 10 mg |
| $MnSO_4 \cdot H_2O$ | 5 mg |
| $H_3BO_3$ | 30 mg |
| $CoSO_4 \cdot 7H_2O$ | 24 mg |
| $CuSO_4 \cdot 5H_2O$ | 5 mg |
| $Na_2MoO_4 \cdot 2H_2O$ | 5 mg |
| $Ca(OH)_2$ | 50 mg |
| Water | 1000 mL |

The composition of the mixed vitamin solution shown in Table 1 is shown in the following Table 3.

TABLE 3

| Composition of Mixed Vitamin Solution | |
|---|---|
| Biotin | 10 mg |
| Cyanocobalamine | 20 mg |
| Calcium pantothenate | 25 mg |
| Thiamine | 50 mg |
| Nicotinic acid | 100 mg |
| Pyridoxamine | 250 mg |
| p-aminobenzoic acid | 500 mg |
| Water | 1000 mL |

This microorganism was inoculated into 20 mL aliquots of the inorganic medium each containing 1 to 8 mg/L of a methylthiotriazine compound (i.e., ametryn, desmetryn, dimethametryn, prometryn, or simetryn), a chlorotriazine compound (i.e., atrazine, propazine, terbuthylazine, or simazine), or a methoxytriazine compound (i.e., atraton) to obtain culture solutions, and was then incubated on a rotary shaker at 30° C. at 120 rpm. One milliliter of each of the culture solutions was sampled at the start of this experiment and after 6 days and centrifuged to obtain a culture supernatant. The culture supernatant was subjected to HPLC to measure the concentration of the triazine compound in the culture supernatant. The measurement results are shown in FIG. 3. As shown in FIG. 3, when measured 6 days after the start of incubation, the concentration of the agrichemical (triazine compound) in each of the culture solutions was equal to or less than the detection limit. From the result, it has become clear that the microorganism according to the present invention has the ability to significantly decompose a methylthiotriazine compound, a chlorotriazine compound, and a methoxytriazine compound.

Further, the strain obtained by a method which will be described later in Example 3 significantly reduced the concentration of simetryn in its culture solution.

A method according to the present invention for decomposing a methylthiotriazine compound, a chlorotriazine compound, and/or a methoxytriazine compound, preferably a method according to the present invention for decomposing at least one selected from the group consisting of simetryn, ametryn, prometryn, dimethametryn, desmetryn, terbutryn, simazine, atrazine, propazine, terbuthylazine, simeton, atraton, and prometon can be carried out by bringing the bacterium according to the present invention belonging to the genus *Nocardioides* having the ability to decompose a methylthiotriazine compound, a chlorotriazine compound, and a methoxytriazine compound into contact with a material containing a methylthiotriazine compound, a chlorotriazine compound, and/or a methoxytriazine compound under conditions where the bacterium according to the present invention can grow. The conditions where the bacterium according to the present invention can grow are preferably achieved by the inorganic medium described above, but are not particularly limited as long as the bacterium can perform the decomposition of a triazine compound. Examples of the material containing a methylthiotriazine compound, a chlorotriazine compound, and/or a methoxytriazine compound include waste agrichemicals, soil, groundwater, and service water containing a methylthiotriazine compound, a chlorotriazine compound, and/or a methoxytriazine compound.

A composition according to the present invention for decomposing at least one selected from the group consisting of methylthiotriazine compounds, chlorotriazine compounds, and methoxytriazine compounds, preferably simetryn, ametryn, prometryn, dimethametryn, desmetryn, terbutryn, simazine, atrazine, propazine, terbuthylazine, simeton, atraton, and prometon contains the triazine compound-decomposing bacterium according to the present invention described above. A carrier allowing the bacterium contained in the composition to grow is not particularly limited as long as it is a material satisfying the conditions where the microorganism according to the present invention can grow. Examples of such a carrier include the above-described medium, a modified medium thereof, and a support for supporting the microorganism according to the present invention. Such a support is not particularly limited as long as it can stably retain the microorganism according to the present invention, and examples thereof include porous materials, more specifically, porous carbonized woody materials, carbonized bamboo materials, and cotton cloth materials enriched with the bacterium according to the present invention or a complex microbial system containing the bacterium according to the present invention. More specific examples of the support include porous materials described in Japanese Patent Application Laid-Open Nos. 10-225288 (Japanese Patent No. 3030370) and 11-318435 (Japanese Patent No. 2904432), disclosures of which are incorporated herein by reference.

An apparatus disclosed in WO 2000/078923 may also be used. In this case, the microorganism according to the present invention is held by a carrier for holding a decomposing bacterium provided in the apparatus.

The use of the bacterium according to the present invention capable of decomposing a methylthiotriazine, a chlorotriazine, and a methylthiotriazine and/or the composition for decomposing a methylthiotriazine compound, a chlorotriazine compound, or a methoxytriazine compound containing the decomposing bacterium according to the present invention makes it possible to detoxify waste agrichemicals containing a methylthiotriazine compound such as simetryn, ametryn, prometryn, dimethametryn, desmetryn, or terbutryn, a chlorotriazine compound such as simazine, atrazine, propazine, or terbuthylazine, and/or a methoxytriazine compound such as simeton, atraton, or prometon or to cleanup an environment such as soil or water (e.g., groundwater or service water) polluted with a methylthiotriazine compound, a chlorotriazine compound, and/or a methoxytriazine compound. A method for decomposing a methylthiotriazine compound, a chlorotriazine compound, and/or a methoxytriazine compound using the decomposing bacterium according to the present invention and/or the composition containing the decomposing bacterium according to the present invention can be carried out by bringing the bacterium according to the present invention belonging to the genus *Nocardioides* having the ability to decompose a methylthiotriazine, a chlorotriazine, and a methoxytriazine or the composition containing the bacterium according to the present invention into contact with a material containing a methylthiotriazine compound, a chlorotriazine compound, and/or a methoxytriazine compound under conditions where the bacterium can grow. According to such a method, it is possible to decompose a methylthiotriazine compound, a chlorotriazine compound, and/or a methoxytriazine compound contained in waste agrichemicals containing a methylthiotriazine compound such as simetryn, ametryn, prometryn, dimethametryn, desmetryn, or terbutryn, a chlorotriazine compound such as simazine, atrazine, propazine, or terbuthylazine, and/or a methoxytriazine compound such as simeton, atraton, or prometon or a material such as soil or water (e.g., groundwater or service water) polluted with a methylthiotriazine compound, a chlorotriazine compound, and/or a methoxytriazine compound using the microorganism according to the present invention so that the waste agrichemicals are detoxified and the material such as soil or water is cleaned up.

Further, the present invention also provides a composition suitable for detoxifying such an environmental pollutant as described above and cleaning up an environment. The composition contains a bacterium belonging to the genus *Nocardioides* having the ability to decompose a methylthiotriazine, a chlorotriazine, and a methoxytriazine and a carrier allowing the bacterium to grow. As such a carrier, the same one as described above with reference to the composition for decomposing a methylthiotriazine compound, a chlorotriazine compound and/or a methoxytriazine compound can be used.

EXAMPLES

Hereinafter, the present invention will be specifically described in more detail with reference to the following examples for illustrating isolation, classification, and identification of the decomposing bacterium according to the present invention and a decomposition experiment of methylthiotriazine compounds, chlorotriazine compounds, and methoxytriazine compounds using the decomposing bacterium according to the present invention. However, the present invention is not limited to these examples.

Example 1

Isolation of Strain MTD22

The present inventors have isolated a *Nocardioides* sp. strain MTD22 as a novel bacterium according to the present invention capable of decomposing a methylthiotriazine, a chlorotriazine, and a methoxytriazine in the following manner. As shown in FIG. 1, 30 to 50 g of soil was placed in a soil layer tank 1 to form an enriching soil layer 2. Then, 200 mL of a sterilized inorganic salt medium containing an appropriate amount of simetryn as a carbon and nitrogen source was pumped out of a solution storage tank 4 and circulated as a circulating solution 3 through the enriching soil layer 2. The composition of the inorganic salt medium used is shown in the following Table

TABLE 4

| Composition of Inorganic Medium 2 | |
| --- | --- |
| $MgSO_4 \cdot 7H_2O$ | 200 mg |
| $K_2HPO_4$ | 1000 mg |
| $FeSO_4 \cdot 7H_2O$ | 50 mg |
| $CaCl_2$ | 20 mg |
| $MnCl_2 \cdot 4H_2O$ | 20 mg |
| $Na_2MoO_4 \cdot 2H_2O$ | 1 mg |
| Water | 1000 mL |

Four sets of the apparatus shown in FIG. 1 were prepared. The circulating solution was circulated in each of the apparatuses, and the concentration of simetryn in the circulating solution was measured by HPLC. The measurement results are shown in FIG. 2. In the graph shown in FIG. 2, the ordinate represents the concentration of simetryn in the circulating solution (which is a relative value calculated by defining the concentration of simetryn in a fresh circulating solution as 1) and the abscissa represents circulation time (day). The arrows shown in FIG. 2 indicate the timing of complete replacement of the circulating solution with fresh one. As can be seen from FIG. 2, the concentration of simetryn in the circulating solution in the apparatus C (which is indicated by an open circle (o) in the graph shown in FIG. 2) was sharply reduced.

Then, two sets of the apparatus shown in FIG. 1 were further prepared, and 2.2 g of a carbonized woody material and about 1 g of the soil sampled from the apparatus C were added to the soil layer tank of each of the apparatuses. These apparatuses were operated for about 1 month, and then one particle of the charcoal (carbonized woody material) was taken out of the apparatus at a time when the carbonized woody material was considered to have become enriched in a simetryn-decomposing bacterium, and was placed in a 500 mL Erlenmeyer flask containing 200 mL of a medium having the composition shown in Table 4 to culture the simetryn-decomposing bacterium at 30° C. with shaking. As a result, simetryn in a culture solution was decomposed little by little. Therefore, in order to reduce the number of kinds of bacteria present in the culture solution, the culture solution was subcultured by a limiting dilution method for about 1 year. More specifically, one part by volume of the culture solution was diluted with nine parts by volume of the inorganic medium to obtain a diluted culture solution, and then one part by volume of the diluted culture solution was further diluted with nine parts by volume of the inorganic medium. Such operation was repeated until a $10^8$-fold diluted culture solution was obtained to create a dilution series. Then, 0.5 mL of each of the thus obtained diluted culture solutions of the dilution series was inoculated into a fresh medium and shaking-cultured at 30° C. Then, the concentration of simetryn in each culture solution was appropriately measured by HPLC to select culture solutions in which decomposition of simetryn was observed. From the selected culture solutions, one culture solution, into which the diluted culture solution of the highest dilution had been inoculated, was further selected, and one part of the selected culture solution was sampled, diluted, and subcultured in the same manner as described above. This operation was repeated every one week to one month.

After repeated subculture for about 1 year, it became possible to completely decompose simetryn in about 1 week even in a highly-diluted subculture solution when the concentration of simetryn was about 20 mg/L. From the result, it was considered that the number of kinds of bacteria present in the culture solution was reduced and the simetryn-decomposing bacterium became dominant. Then, isolation of the simetryn-decomposing bacterium was performed in the following manner.

From the above culture solutions, one culture solution, into which a diluted culture solution of the highest dilution had been inoculated, was selected, and the selected culture solution was streak-inoculated onto a R2A agar medium with a 10 μL-inoculating loop and then statically cultured at 30° C. Then, a single colony formed on the R2A agar medium was picked up with an inoculating needle, and again streak-inoculated onto a fresh R2A medium and statically cultured at 30° C. Then, cells growing on the R2A agar medium were collected with an inoculating loop, inoculated into 20 mL of the inorganic medium containing 25 mg/L of simetryn contained in a 100 mL Erlenmeyer flask, and shaking-cultured at 30° C. A temporal change in the concentration of simetryn in the culture medium was monitored by HPLC, and as a result, simetryn was completely decomposed in two days. However, it was considered that isolation of the simetryn-decomposing bacterium was not sufficient. Therefore, one part of the culture solution was sampled and diluted to $10^8$-fold with the inorganic medium in the same manner as described above to create a dilution series. Then, 100 μL of each diluted culture solution of the dilution series was inoculated onto a R2A agar medium and statically cultured at 30° C. Then, a single colony formed on the medium was picked up with an inoculating loop, streak-inoculated onto another R2A medium, and statically cultured at 30° C. Then, cells growing on the R2A agar medium were collected with an inoculating loop, inoculated into 20 mL of the inorganic medium containing 25 mg/L of simetryn contained in a 100 mL Erlenmeyer flask, and shaking-cultured at 30° C. A temporal change in the concentration of simetryn in the culture medium was monitored by HPLC, and as a result, an isolated strain capable of decomposing simetryn was identified and named strain MTD22.

Example 2

Bacteriological Studies of Strain MTD22

In order to determine the taxonomic position of the strain MTD22 isolated in Example 1, morphological properties, growth on medium, physiological properties, and biochemical properties of the strain MTD22 were analyzed at NCIMB Japan. As a result, the strain MTD22 had the following bacteriological characteristics.

A. Morphological characteristics (culture medium: R2A agar (manufactured by Difco), incubation temperature: 30° C., incubation time: 48 hours)
(1) Cell morphology: cocci
(2) Size: 1.0 to 1.2 μm
(3) Spore formation: None
(4) Mobility: None B. Colony morphology (culture medium: R2A agar (manufactured by Difco), incubation temperature: 30° C., incubation time: 48 hours)
(5) Colony diameter: 1.0 mm
(6) Color: Slightly yellow
(7) Shape: Circular
(8) Elevation: Lens shape
(9) Margin: Entire
(10) Surface profile: Smooth
(11) Transparency: Opaque
(12) Viscosity: Butter-like C. Physiological properties
(13) Gram stain: +
(14) Growth at 37° C.: −
(15) Growth at 25° C.: +
(16) Catalase: +
(17) Oxidase: −
(18) Acid/gas generation from glucose: −/−
O/F test: −/−

D. Biochemical property test (performed using API Coryne manufactured by SYSMEX bioMerieux Co., Ltd.)
(20) Nitrate reduction: −
(21) Pyrazine amidase: +
(22) Pyrrolidonyl arylamidase: −
(23) Alkaline phosphatase: −
(24) β-glucuronidase: −
(25) (β-galactosidase: −
(26) α-glucosidase: +
(27) N-acetyl-β-glucosaminidase: −
(28) Esculin: +
(29) Urease: −
(30) Gelatin hydrolysis: +
(31) Glucose assimilation: −
(32) Ribose assimilation: −
(33) Xylose assimilation: −
(34) Mannitol assimilation: −
(35) Maltose assimilation: −
(36) Lactose assimilation: −
(37) Sucrose assimilation: −
(38) Glycogen assimilation: −

Based on the results, the strain MTD22 according to the present invention was identified using the Bergey's Manual (Bergey's Manual of Systematic Bacteriology Vol. 2 (1984)) and estimated to be a species of coryneform bacterium. The group of coryneform bacteria includes various bacteria, and therefore it was difficult to classify and identify the strain MTD22 based on only its bacteriological characteristics determined by the analyses described above. Therefore, genetic classification of the strain MTD22 was made in the following manner based on the base sequence of its 16S rRNA gene.

(1) DNA was prepared from cells of the strain MTD22 using DNeasy Tissue Kit (manufactured by QIAGEN).

(2) The 16S rRNA gene fragment of the strain MTD22 was amplified by PCR using the DNA prepared in (1) as a template DNA and known primers for amplifying a eubacterial 16S rRNA gene, and amplified DNA was purified using QIAquick PCR Purification Kit (manufactured by QIAGEN).

(3) Cycle sequence reaction was carried out using the purified DNA as a template DNA and fluorescently-labeled known primers for analyzing the base sequence of a eubacterial 16S rRNA gene to determine the base sequence of the DNA using a DNA sequencer SQ5500E (manufactured by Hitachi).

The base sequence of a part of the 16S rRNA gene of the strain MTD22 (1477 bases) determined by the above operation is shown in SEQ ID No. 1. The base sequence of a part of the 16S rRNA gene of the strain MTD22 shown in SEQ ID No. 1 was compared with the base sequences of 16S rRNA genes of other microorganisms registered in the DNA base sequence database (GenBank) by the FASTA method using Genetics PDB (manufactured by Genetics) to determine sequence identity. As a result, the degree of identity of the strain MTD22 with *Marmoricola aurantiacus* was 97.4%, and the degree of identity of the strain MTD22 with *Marmoricola* sp. strain CNJ 872 PL04 was 97.1%. However, the strain MTD22 and *Marmoricola aurantiacus* were discordant in some phenotypic characters such as colony color and casein degradability, and the strain MTD22 was similar to bacteria belonging to the genus *Nocardioides* rather than to *Marmoricola aurantiacus*. Based on the above results, the present inventors have identified the isolated strain according to the present invention as a novel *Nocardioides* sp. strain MTD22. The strain MTD22 was deposited on Aug. 11, 2006 in the International Patent Organism Depositary of the National Institute of Advanced Industrial Science and Technology (Tsukuba Central 6, 1-1, Higashi 1-chome, Tsukuba-shi, Ibaraki, Japan) under the accession number of FERM P-20989, and was then transferred on Jul. 4, 2007 from the International Patent Organism Depositary of the National Institute of Advanced Industrial Science and Technology (Tsukuba Central 6, 1-1, Higashi 1-chome, Tsukuba-shi, Ibaraki, Japan) to the International Depositary Authority and assigned the accession number FERM BP-10849.

Example 3

Decomposition of Methylthiotriazine Compounds, Chlorotriazine Compounds, and a Methoxytriazine Compound Using Strain MTD22

The present inventors have examined the ability of the strain MTD22 to decompose triazine compounds in the following manner. Twenty milliliters aliquots of an inorganic liquid medium each containing about 1 to 8 mg/L of a methylthiotriazine compound (i.e., ametryn, desmetryn, dimethametryn, prometryn, or simetryn), a chlorotriazine compound (i.e., atrazine, simazine, propazine, or terbuthylazine), or a methoxytriazine compound (i.e., atraton) were dispensed into 100 mL Erlenmeyer flasks. On the other hand, the strain MTD22 was statically cultured on a R2A agar medium at 30° C., and then colonies growing on the agar medium were collected with an inoculating loop and suspended in 1.5 mL of the inorganic medium to obtain a suspension. Then, 100 μL of the suspension was inoculated into each of the aliquots of inorganic liquid medium and cultured on a rotary shaker at 30° C. at 120 rpm. The concentration of each triazine compound was measured by HPLC at the start of this experiment (Day 0) and after 6 days (Day 6).

The measurement results are shown in FIG. 3. In the graph shown in FIG. 3, the ordinate represents the concentration of each triazine compound, the abscissa represents the type of triazine compound under test and time, and the filled circle (●) represents the concentration of each agrichemical (triazine compound) measured at the start of the experiment or after 6 days.

As can be seen from FIG. 3, the triazine compound contained in each culture solution was completely decomposed by the strain MTD22 within 6 days. From the result, it has been found that the strain MTD22 has the ability to quickly decompose a methylthiotriazine compound, a chlorotriazine compound, and a methoxytriazine compound.

INDUSTRIAL APPLICABILITY

The present invention provides a novel bacterium capable of decomposing a methylthiotriazine compound, a chlorotriazine compound, and a methoxytriazine compound which are heavily used as agrichemicals, a composition containing such a novel bacterium, and a method for decomposing a methylthiotriazine compound, a chlorotriazine compound, and a methoxytriazine compound using the bacterium or the composition. According to the present invention, it is possible to decompose and detoxify waste agrichemicals and excess methylthiotriazine compound, chlorotriazine compound, and methoxytriazine compound remaining in an environment. This contributes to environmental cleanup to provide clean soil and water containing no toxic residues.

Sequence Listing Free Text

SEQ ID No. 1: 1477 bases of the 16S rRNA gene of the decomposing bacterium strain MTD22 according to the present invention

The invention claimed is:

1. An isolated bacterium belonging to the genus *Nocardioides* which has a 16S rRNA gene containing a DNA comprising the base sequence of SEQ ID NO:1 and has an ability to decompose a methylthiotriazine compound, a chlorotriazine compound, and a methoxytriazine compound.

2. An isolated bacterium, *Nocardioides* sp. strain MTD22 (accession number: FERM P-20989; accession number: FERM BP-10849) having an ability to decompose a methylthiotriazine compound, a chlorotriazine compound, and a methoxytriazine compound.

3. A method for decomposing a methylthiotriazine compound, a chlorotriazine compound, and/or a methoxytriazine compound using the bacterium according to claim 1.

4. The decomposing method according to claim 3, wherein the methylthiotriazine compound is at least one selected from the group consisting of simetryn, ametryn, dimethametryn, desmetryn, terbutryn, and prometryn.

5. The decomposing method according to claim 3, wherein the chlorotriazine compound is at least one selected from the group consisting of atrazine, simazine, propazine, and terbuthylazine.

6. The decomposing method according to claim 3, wherein the methoxytriazine compound is at least one selected from the group consisting of atraton, simeton, and prometon.

7. A method for cleaning up soil, groundwater, and/or service water polluted with a methylthiotriazine compound, a chlorotriazine compound, and/or a methoxytriazine compound using the bacterium according to claim 1.

8. A triazine compound-decomposing agent for decomposing a methylthiotriazine compound, a chlorotriazine compound, and/or a methoxytriazine compound comprising: at least one bacterium according to claim 1; and a carrier allowing the bacterium to grow.

9. An agent for cleaning up soil, groundwater, and/or service water polluted with a methylthiotriazine compound, a chlorotriazine compound, and/or a methoxytriazine compound comprising: at least one bacterium according claim 1; and a carrier allowing the bacterium to grow.

10. A method for decomposing a methylthiotriazine compound, a chlorotriazine compound, and/or a methoxytriazine compound using the bacterium according to claim 2.

11. The decomposing method according to claim 10, wherein the methylthiotriazine compound is at least one selected from the group consisting of simetryn, ametryn, dimethametryn, desmetryn, terbutryn, and prometryn.

12. The decomposing method according to claim 10, wherein the chlorotriazine compound is at least one selected from the group consisting of atrazine, simazine, propazine, and terbuthylazine.

13. The decomposing method according to claim 10, wherein the methoxytriazine compound is at least one selected from the group consisting of atraton, simeton, and prometon.

14. A method for cleaning up soil, groundwater, and/or service water polluted with a methylthiotriazine compound, a chlorotriazine compound, and/or a methoxytriazine compound using the bacterium according to claim 2.

15. A triazine compound-decomposing agent for decomposing a methylthiotriazine compound, a chlorotriazine compound, and/or a methoxytriazine compound comprising: at least one bacterium according to claim 2; and a carrier allowing the bacterium to grow.

16. An agent for cleaning up soil, groundwater, and/or service water polluted with a methylthiotriazine compound, a chlorotriazine compound, and/or a methoxytriazine compound comprising: at least one bacterium according to claim 2; and a carrier allowing the bacterium to grow.

* * * * *